United States Patent [19]

Van Hout et al.

[11] Patent Number: 5,698,481
[45] Date of Patent: Dec. 16, 1997

[54] STERILIZATION WRAP MATERIAL

[75] Inventors: Leslie Hope Van Hout, Roswell; Bernard Cohen, Berkeley Lake; Lee Kirby Jameson, Roswell, all of Ga.

[73] Assignee: Kimberly-Clark Worldwide, Inc., Neenah, Wis.

[21] Appl. No.: 736,455

[22] Filed: Oct. 24, 1996

Related U.S. Application Data

[60] Continuation of Ser. No. 398,252, Mar. 3, 1995, abandoned, which is a division of Ser. No. 321,487, Oct. 12, 1994, abandoned.

[51] Int. Cl.$^6$ .............................. B32B 3/30; B32B 27/12
[52] U.S. Cl. .................... 442/394; 442/398; 442/400; 442/401
[58] Field of Search .................... 442/394, 398, 442/401, 400

[56] References Cited

U.S. PATENT DOCUMENTS

| | | | |
|---|---|---|---|
| 2,718,666 | 9/1955 | Knox | 18/57 |
| 2,841,202 | 7/1958 | Hirschy | 154/1.7 |
| 3,016,599 | 1/1962 | Perry, Jr. | 28/78 |
| 3,035,475 | 5/1962 | Renke et al. | 87/1 |
| 3,041,915 | 7/1962 | Ryffel | 87/12 |
| 3,341,394 | 9/1967 | Kinney | 161/72 |
| 3,484,835 | 12/1969 | Troustine et al. | 428/154 |
| 3,655,862 | 4/1972 | Dorschner et al. | 264/290 |
| 3,692,618 | 9/1972 | Dorschner et al. | 161/72 |
| 3,704,198 | 11/1972 | Prentice | 161/148 |
| 3,705,068 | 12/1972 | Dobo et al. | 156/441 |

(List continued on next page.)

FOREIGN PATENT DOCUMENTS

| | | |
|---|---|---|
| 0 256 717 | 2/1988 | European Pat. Off. |
| 0 295 694 | 12/1988 | European Pat. Off. |
| 0 308 205 | 3/1989 | European Pat. Off. |
| 0 505 027 A1 | 2/1992 | European Pat. Off. |
| 0 505 027 | 9/1992 | European Pat. Off. |
| 2200307 | 4/1974 | France |
| 37 24 510 | 2/1989 | Germany |
| 40 03 764 | 8/1991 | Germany |
| 3030934 | 2/1991 | Japan |
| 3053931 | 3/1991 | Japan |
| 2 095 616 | 10/1982 | United Kingdom |
| 2 132 939 | 7/1984 | United Kingdom |
| 85/05373 | 12/1985 | WIPO |
| 91/11374 | 8/1991 | WIPO |

OTHER PUBLICATIONS

V.A. Wente, "Superfine Thermoplastic Fibers", *Industrial and Engineering Chemistry*, vol. 48, No. 8, pp. 1342–1346 (1956).

V.A. Wente, et al., "Manufacture of Superfine Organic Fibers" Navy Res. Lab., Wash., D.C., NRL eport 4364 (111437), May 25, 1954 U.S. Department of Commerce, Office of Technical Service.

R.R. Butin, et al., "Melt Blowing—A One–Step Web Process for New Nonwoven Products", *Journal of the Technical Association of the Pulp and Paper Industry*, vol. 56, No. 4, pp. 74–77 (1973).

*Primary Examiner*—Kathleen Choi
*Attorney, Agent, or Firm*—William E. Maycock

[57] ABSTRACT

A polyolefin film for use as a sterilization wrap material which includes a film with a thickness of from about 0.005 mm to about 0.2 mm and having a plurality of discontinuous thinned regions. The thinned regions constitute at least about 25 percent of the surface area of the film. The thickness and area of the thinned regions are adapted to permit the passage of steam and water vapor through the film during steam sterilization. The film is made by a method which involves extruding a molten polyolefin film at a first temperature and passing the molten film through a nip. The nip includes an anvil roll and a pattern roll. The anvil roll has a smooth surface and the surface of the pattern roll is maintained at a temperature which is at least about 150° C. lower than the first temperature and is selected to prevent sticking of the film to either roll.

13 Claims, 1 Drawing Sheet

U.S. PATENT DOCUMENTS

| | | | |
|---|---|---|---|
| 3,755,527 | 8/1973 | Keller et al. | 264/210 |
| 3,802,817 | 4/1974 | Matsuki et al. | 425/66 |
| 3,817,807 | 6/1974 | Braun et al. | 156/181 |
| 3,832,267 | 8/1974 | Chia-Seng Liu | 161/116 |
| 3,849,241 | 11/1974 | Butin et al. | 161/169 |
| 3,851,034 | 11/1974 | Harmon et al. | 264/147 |
| 3,853,651 | 12/1974 | Porte | 156/73.6 |
| 3,932,682 | 1/1976 | Loft et al. | 428/296 |
| 3,978,185 | 8/1976 | Butin et al. | 264/93 |
| 4,041,203 | 8/1977 | Brock et al. | 428/157 |
| 4,064,605 | 12/1977 | Akiyama et al. | 28/103 |
| 4,091,140 | 5/1978 | Harmon | 428/288 |
| 4,100,319 | 7/1978 | Schwartz | 428/171 |
| 4,100,324 | 7/1978 | Anderson et al. | 428/288 |
| 4,118,531 | 10/1978 | Hauser | 428/224 |
| 4,196,245 | 4/1980 | Kitson et al. | 428/198 |
| 4,308,303 | 12/1981 | Mastroianni | 428/90 |
| 4,340,563 | 7/1982 | Appel et al. | 264/518 |
| 4,344,999 | 8/1982 | Gohlke | 428/212 |
| 4,379,192 | 4/1983 | Wahlquist et al. | 428/156 |
| 4,405,297 | 9/1983 | Appel et al. | 425/72 |
| 4,434,204 | 2/1984 | Hartman et al. | 428/198 |
| 4,472,328 | 9/1984 | Sugimoto et al. | 264/41 |
| 4,508,113 | 4/1985 | Malaney | 128/132 |
| 4,546,029 | 10/1985 | Cancio et al. | 428/141 |
| 4,596,738 | 6/1986 | Metcalfe et al. | |
| 4,609,584 | 9/1986 | Cutler et al. | 428/156 |
| 4,618,524 | 10/1986 | Groitzsch et al. | 428/198 |
| 4,622,259 | 11/1986 | McAmish et al. | 428/171 |
| 4,627,811 | 12/1986 | Greiser et al. | 428/72 |
| 4,644,045 | 2/1987 | Fowells | 526/348 |
| 4,645,501 | 2/1987 | Teed | 604/390 |
| 4,657,804 | 4/1987 | Mays et al. | 428/212 |
| 4,663,220 | 5/1987 | Wisneski et al. | 428/221 |
| 4,726,976 | 2/1988 | Karami et al. | |
| 4,756,786 | 7/1988 | Malaney | 156/308.2 |
| 4,758,239 | 7/1988 | Yeo et al. | 604/366 |
| 4,761,326 | 8/1988 | Barnes et al. | 428/219 |
| 4,777,073 | 10/1988 | Sheth | 428/155 |
| 4,815,714 | 3/1989 | Douglas | 264/22 |
| 4,828,556 | 5/1989 | Braun et al. | 604/365 |
| 4,863,785 | 9/1989 | Berman et al. | 428/218 |
| 4,892,779 | 1/1990 | Leatherman | 428/220 |
| 4,904,520 | 2/1990 | Dumas et al. | 428/212 |
| 4,921,653 | 5/1990 | Aoyama et al. | |
| 4,929,303 | 5/1990 | Sheth | |
| 4,943,475 | 7/1990 | Baker et al. | 428/246 |
| 4,975,469 | 12/1990 | Jacoby et al. | 521/84.1 |
| 4,978,486 | 12/1990 | Ito et al. | 264/41 |
| 5,015,521 | 5/1991 | Fuji et al. | 428/220 |
| 5,019,422 | 5/1991 | Rose et al. | 427/245 |
| 5,059,454 | 10/1991 | Todd et al. | 427/259 |
| 5,089,075 | 2/1992 | Sonoda | 156/244 |
| 5,188,885 | 2/1993 | Timmons et al. | |
| 5,202,173 | 4/1993 | Wu et al. | 428/131 |
| 5,344,862 | 9/1994 | Nohr et al. | 524/269 |

STERILIZATION WRAP MATERIAL

This application is a continuation of application Ser. No. 08/398,252 entitled "STERILIZATION WRAP MATERIAL" and filed in the U.S. Patent and Trademark Office on Mar. 3, 1995 now abandoned, which is a divisional application of Ser. No. 08/321,487, filed Oct. 12, 1994, now abandoned. The entirety of this application is hereby incorporated by reference.

BACKGROUND OF THE INVENTION

The present invention relates to a sterilization wrap material.

Surgical instruments and materials intended for use during a surgical procedure must be provided to the surgeon in a sterile condition. In theory, it is possible to sterilize the various surgical instruments and materials in the operating suite immediately prior to presentation to the surgeon. However, such a procedure is not practical because of the time required to complete the sterilization process. Moreover, the procedure would not accommodate instrument needs for unanticipated or emergency surgical procedures, particularly where the life of the patient may be at risk.

Surgical instruments and materials almost universally are sterilized in advance of surgery and stored until needed. Sterilization most commonly is carried out by pressurized, superheated steam in a sterilizing autoclave or sterilizer, although a variety of procedures may be employed. For example, one or more of such articles may be wrapped in at least one sheet of a porous material (i.e., a sterilization wrap), such as paper, toweling, muslin, or a disposable nonwoven fabric. The resulting package of wrapped articles is sealed with tape and placed in a sterilizer. Pressurized superheated steam is admitted into the sterilizer, typically at a pressure of about 1 kilogram per square centimeter (kg/cm$^2$) and a temperature of about 135° C. The steam penetrates the porous material of the package to contact and sterilize the articles contained within. Some sterilizers provide for the removal of air before introduction of the steam and/or the removal of moisture after autoclaving by means of a vacuum-drying cycle. With most of such sterilizers, atmospheric pressure is restored within the autoclave by admitting ambient air prior to removal of the package.

While relatively simple, the above procedure did not make the surgical instruments and materials readily accessible to the surgeon in an orderly manner. Unless multiple layers of wrapping were employed, contamination by microorganisms or particles of wrapping was a frequent occurrence. Furthermore, the shelf life of the sterilized package was relatively short. That is, contamination by microorganisms could occur over time, even without tears or breaks in the wrapping. Consequently, resterilization often was required before the articles could be used. Finally, the procedure frequently resulted in the loss of or damage to expensive instruments. The wrapping from the opened packed typically was spread out on a table in an operating room and the instruments were placed on it after use. The wrapping subsequently was collected for disposal or reuse. Unless the instruments were meticulously removed from the wrapping, loss or damage often occurred.

Some of the problems associated with the foregoing procedure were alleviated by the use of a shallow tray, in which the appropriate number and selection of surgical instruments and materials are placed. The tray typically is fabricated from stainless steel so as to withstand the harsh environment inside the sterilizer. The tray with the surgical instruments and materials is wrapped in more than one layer of fabric material to form a bundle having an inner wrapping and an outer wrapping which is suitably secured and marked for subsequent identification. The bundle then is sterilized as described above, removed from the sterilizer, and stored for future use.

Once the bundle is removed from the sterilizer, the outer surface or outer wrapping no longer is sterile but, if properly handled, the internal contents of the bundle generally remain sterile for a reasonable amount of time. Accordingly, the outer wrapping is removed and the sterile, inner wrapped bundle is introduced into the sterile environment in the surgical suite. This technique is well known and has been developed and refined over the years.

Several problems have been encountered using shallow trays. For example, the surgical instruments and materials slide easily across the tray into injurious contact with the tray and also the wrapping material. This injurious contact not only can damage certain instruments but also can cut the wrapping material which destroys the integrity of the wrap and also generates lint debris which tends to cling to the instruments. Further, the stainless steel trays are heavy and frequently have sharp edges or corners which significantly increase the likelihood that the wrapping material will be torn or otherwise abraded when the tray contacts a hard surface.

Improvements in tray design helped to alleviate some of the problems encountered during the use of the shallow trays. For example, some improved trays, typically made of metal or plastic, generally are deeper and often employ lids. The trays are wrapped and sterilized as already described. However, the instruments can be organized for presentation and the tray provides a receptacle for the collection of used instruments. Alternatively, deeper containers are formed from a nonwoven material which has been treated with a resin, thereby giving the container sufficient rigidity to permit its use in the same way as a metal or plastic container. The nonwoven material remains porous, thereby facilitating sterilization, but still serves as a barrier to microorganisms. Still other containers have been developed which do not require a sterilization wrap.

The wrapping material historically has been obtained from a woven fabric prepared from natural fibers such as cotton or linen. Recent advances have incorporated fabrics woven with synthetic fibers as well as paper and blends of fibers and paper. Nonwoven fabrics also have been introduced, some of which constitute multiple-layer laminates. An example of one laminate is a polypropylene meltblown nonwoven web sandwiched between two polypropylene spunbonded nonwoven webs. Each material is intended to be sufficiently porous to allow passage of a sterilizing gas while inhibiting the migration of microorganisms.

Thus, wrapping materials can be considered to be a specialized group of the so-called breathable barriers. Such barriers often are, or include, films which find use in such personal care items as disposable diapers, feminine care products, and the like. Some examples, by way of illustration only, are:

(1) a film of uniform thickness is obtained by stretching on a series of smooth-surfaced, tension-applying rolls a film having beaded edges;

(2) a breathable or porous film is prepared by stretching a highly filled film which has been embossed to impose a pattern of different film thicknesses therein, a highly filled film which also contains a liquid or waxy hydrocarbon polymer, or a film obtained by blow-extruding a composition consisting of a linear polyethylene, filler, and a radical forming agent;

(3) a film is either embossed in a defined manner and biaxialy drawn in a range of from about 2.5 times to about 5.0 times or abraded by passing the film through at least one set of at least two cooperating nip rollers, each nip roller having an abrasive grit surface, with the abraded film optionally subjected to a corona treatment;

(4) a multilayer composite fabric material consists of a woven or nonwoven fabric support, a microporous membrane layer, and an ultrathin permselective surface coating, and optionally an intermediate sealing layer and a protective top layer;

(5) an impervious absorbent barrier fabric consists of a meltblown nonwoven web joined to an impervious polymeric film by point bonding under the application of heat and pressure, in which meltblown nonwoven web optionally may be overlaid with a spunbonded nonwoven web;

(6) a breathable barrier includes a porous sheet having on one side a continuous film of a water-soluble polymeric material such as poly(vinyl alcohol), which barrier optionally may have joined to either the film or the other side of the porous sheet a porous nonwoven web;

(7) a waterproof water-vapor-permeable laminated structure is obtained by extrusion laminating a thermoplastic resin layer on a porous base material;

(8) a nonwoven medical fabric is obtained by thermally point bonding a meltblown nonwoven web;

(9) a sterilization wrap material consists of a nonwoven textile-type substrate, such as a spunbonded nonwoven web, coated with a continuous network of an open cell microporous film that forms a network of interconnected cells distributed among and covering nearly the entire surface of the substrate; and

(10) sterilization wrap or microfine fiber laminates consist of a middle meltblown nonwoven web sandwiched between two spunbonded nonwoven webs, a meltblown nonwoven web welded to a nonwoven web of discontinuous fibers, a meltblown nonwoven web bonded to a layer of conjugate fibers having a low melting sheath and a high melting core, or a three-ply hydrophobic microfine fiber structure (e.g., three meltblown layers) sandwiched between and bonded to two layers of conjugate fibers having a low melting sheath and a high melting core.

Prior efforts at improving breathable barrier notwithstanding, opportunities still remain for improvements in sterilization wrap materials, particularly with respect to both barrier properties and strength, e.g., resistance to tearing and abrasion.

SUMMARY OF THE INVENTION

The present invention addresses some of the difficulties and problems discussed above by providing a polyolefin film for use as a sterilization wrap material which includes a film with a thickness of from about 0.005 mm to about 0.2 mm and having a plurality of thinned regions. The thinned regions may be continuous, i.e., interconnected, or discontinuous. When the thinned regions are discontinuous, the film may be described as consisting of a plurality of thinned regions which are separated by interconnected or continuous raised (relative to the thinned regions) ridges or lands. The thinned regions permit the passage of steam and water vapor through the film, while the raised ridges or lands provide film integrity by blocking the propagation of tears in the film.

In general, the thickness and area of the thinned regions (as a percentage of the total surface area of the film) are adapted to permit the passage of steam through the film during a steam exposure step and the passage of water vapor through the film during a drying step. As a practical matter, the thinned regions will constitute at least about 25 percent of the surface area of the film. For example, the thinned regions may constitute from about 25 to about 70 percent of the area of the film. However, the thinned regions may constitute lower or higher percentages of the area of the film, depending upon the thickness of the film. As another example, the thickness of the thinned regions may be in a range of from about 75 to about 15 percent of the thickness of the film. As still another example, the thinned regions may constitute a repeating pattern having no more than about 40 lines per centimeter (lines per cm). As yet another example, the thinned regions may constitute a repeating pattern having from about 40 lines per cm to about 15 lines per cm.

The polyolefin film of the present invention may be utilized by itself or as a component, or layer, of a multilayer laminate structure. For example, the film may be joined to a nonwoven web. Examples of nonwoven webs which may be employed include, by way of illustration only, nonwoven webs prepared by such processes as meltblowing, coforming, spunbonding, carding, air laying, and wet laying. Meltblown and spunbonded nonwoven webs are particularly desirable. Spunbonded nonwoven webs are especially useful as they impart greater strength and abrasion resistance to the laminate.

As another example, the laminate may include at least three layers, in which case the film desirably is located between the two other layers. Again, the other two layers desirably are nonwoven webs, especially meltblown and spunbonded nonwoven webs. More desirably, both nonwoven webs will be spunbonded nonwoven webs.

The film is prepared by a method which involves extruding a molten polyolefin film at a first temperature and passing the molten film through a nip comprising an anvil roll and a pattern roll, wherein the anvil roll has a smooth surface and the surface of the pattern roll is maintained at a second temperature which is at least about 150° C. lower than the first temperature and selected to prevent sticking of the film to either roll. For example, the second temperature may be in a range of from about 10° C. to about 50° C. As another example, the second temperature may be in a range of from about 10° C. to about 35° C. As a further example, the second temperature may be in a range of from about 10° C. to about 25° C.

In general, the temperature of the surface of the pattern roll may be maintained at a desired temperature by any means known to those having ordinary skill in the art. As a practical matter, such temperature is readily maintained by circulating a cooling fluid, such as water, through the pattern roll.

The distance between the anvil roll and the pattern roll may selected to give a thickness to the film emerging from the nip of from about 0.005 mm to about 0.2 mm. Other factors affecting film thickness include the velocity of the nip, the volume of molten polymer or extrudate entering the nip which is a function of the extrusion pressure and the extrusion gap or thickness of the molten film as it emerges from the die, and the velocity of the take-up roll.

The surface of the pattern roll may have a plurality of either discontinuous depressions or discontinuous protrusions. When the pattern roll has discontinuous depressions, the film will have continuous thinned regions. Conversely, when the pattern roll has discontinuous protrusions, the film will have discontinuous thinned regions. In either case, the surface area of the depressions or protrusions will constitute at least about 25 percent of the surface area of the pattern roll. When present, the protrusions typically will have a protrusion distance which is a range of from about 15 to about 75 percent of the distance between the anvil roll and the pattern roll.

If desired, a sheet material, such as a nonwoven web, may be joined to either surface of the film after it emerges from the nip. Alternatively two or more sheet materials may be joined to the film. Joining may be accomplished by any known means, such as adhesives, ultrasonic bonding, and the like. The sheet material may be a nonwoven web. For example, the nonwoven web may be a meltblown or spunbonded nonwoven web.

DETAILED DESCRIPTION OF THE INVENTION

Figure 1:
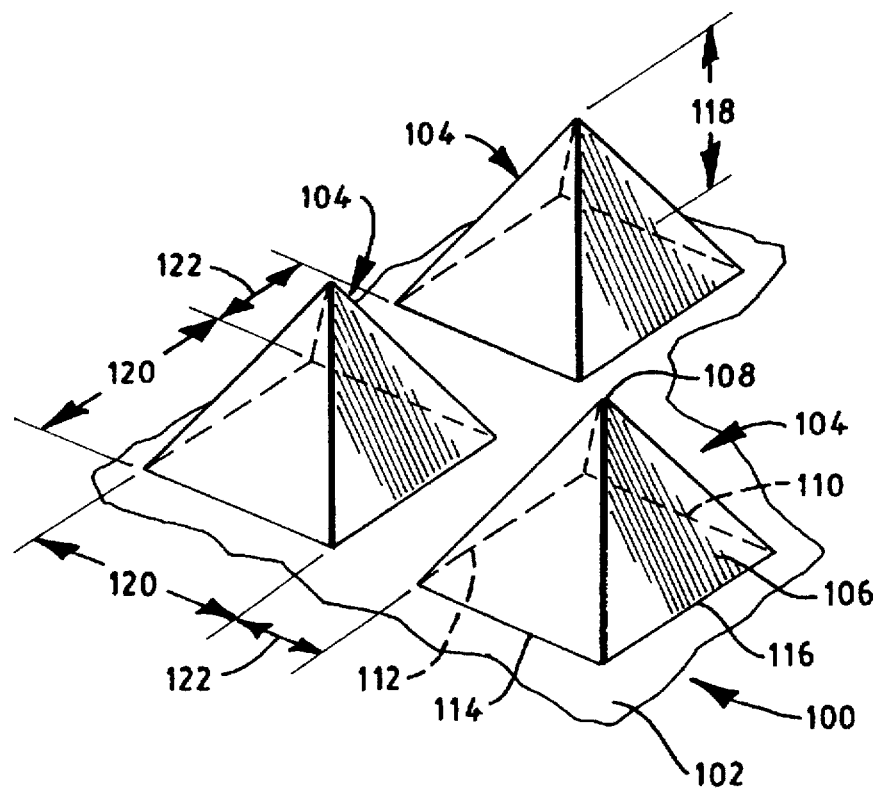
FIG. 1 is a perspective view of a portion of a first pattern roll used in the examples, illustrating pyramidal depressions in the surface of the roll.

The term "polyolefin" is used herein to mean any thermoplastic polyolefin which can be used for the preparation of films. Examples of thermoplastic polyolefins include polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like.

By way of example, polyolefins may be those which contain only hydrogen and carbon atoms and which are prepared by the addition polymerization of one or more unsaturated monomers. Examples of such polyolefins include, among others, polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polystyrene, and the like. In addition, the term "polyolefin" is meant to include blends of two or more polyolefins and random and block copolymers prepared from two or more different unsaturated monomers.

The term "steam sterilization" is used herein to mean any steam sterilization process which includes a steam exposure step and a drying step. The drying step may be accomplished under reduced pressure, i.e., under a vacuum. Sterilization most commonly is carried out by pressurized, superheated steam in a sterilizing autoclave or sterilizer; the terms "sterilizing autoclave" and "sterilizer" are used interchangeably throughout this specification. As noted earlier, the pressurized superheated steam typically is admitted into the sterilizer at a pressure of about 1 kg/cm$^2$ and a temperature of at least about 121° C.

As used herein, the term "nonwoven web" means a web prepared by a traditional melt-extrusion process from a thermoplastic polymer, which process typically involves melting the thermoplastic polymer, extruding the molten polymer through a plurality of orifices to form a plurality of threadlines or filaments, attenuating the filaments by entrainment in a rapidly moving first stream of gas, cooling the filaments with a second stream of gas, and randomly depositing the attenuated filaments, or fibers, on a moving foraminous surface. The most common and well known of these processes are meltblowing, coforming, and spunbonding. The term also includes bonded, carded webs.

Meltblowing references include, by way of example, U.S. Pat. Nos. 3,016,599 to Perry, Jr., 3,704,198 to Prentice, 3,755,527 to Keller et al., 3,849,241 to Butin et al., 3,978,185 to Butin et al., and 4,663,220 to Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973).

Coforming references (i.e., references disclosing a meltblowing process in which fibers or particles are commingled with the meltblown fibers as they are formed) include U.S. Pat. Nos. 4,100,324 to Anderson et al. and 4,118,531 to Hauser.

Finally, spunbonding references include, among others, U.S. Pat. Nos. 3,341,394 to Kinney, 3,655,862 to Dorschner et al., 3,692,618 to Dorschner et al., 3,705,068 to Dobo et al., 3,802,817 to Matsuki et al., 3,853,651 to Porte, 4,064,605 to Akiyama et al., 4,091,140 to Harmon, 4,100,319 to Schwartz, 4,340,563 to Appel and Morman, 4,405,297 to Appel and Morman, 4,434,204 to Hartman et al., 4,627,811 to Greiser and Wagner, and 4,644,045 to Fowells.

The term "scrim" is used herein to mean a material having a set of spaced warp threads which extend substantially in the longitudinal or machine direction and a set of spaced fill threads which extend across the warp threads substantially in the cross or transverse direction. The scrim may be a woven or a nonwoven material, such as the materials described in, for example, U.S. Pat. Nos. 3,041,915 to Ryffel and 3,035,475 to Rinke and Windemuth, and 2,841,202 to Hirschy and 3,817,807 to Braun and Schwoerer, respectively.

The film of the present invention has a thickness of from about 0.005 mm to about 0.2 mm and a plurality of thinned regions. The thickness and area of the thinned regions are adapted to permit the passage of steam through the film during the steam exposure step and the passage of water vapor through the film during the drying step. By way of example, the film may have a thickness of from about 0.01 mm to about 0.1 mm. As another example, the film may have a thickness of from about 0.01 mm to about 0.05 mm. When the thinned regions are discontinuous, the film possesses the added advantage of maintaining film integrity before, during, and after steam sterilization. The raised ridges or lands which separate the discontinuous thinned regions block the propagation of tears in the film.

In order to facilitate the passage of steam through the film during the steam exposure step and the passage of water vapor through the film during the drying step, the thinned regions typically will comprise at least about 25 percent of the surface area of the film, calculated as the difference between the total surface area of the film and the surface area of the nonthinned area. For example, the area of the thinned regions may be in a range of from about 25 to about 70 percent of the surface area of the film. As already pointed out, the thinned regions may constitute lower or higher percentages of the area of the film, depending upon the thickness of the film. Similarly, the thickness of the thinned regions may be in a range of from about 75 to about 15 percent of the thickness of the film.

It should be noted that the calculation of the area of the thinned regions typically is an approximation. Such calculation will be precise only when the sides of the depressions or protrusions are normal to the surface of the pattern roll and the ends of the depressions or protrusions terminate in surfaces which are coplanar with the surface of the pattern roll. When the openings of the depressions or the bases of the protrusions are separated, i.e., not touching the openings of adjacent depressions or the bases of adjacent protrusions, respectively, the area of the thinned regions conveniently is taken as the sum of the areas of the openings of the depressions or the bases of the protrusions. If the openings of the depressions or the bases of the protrusions are touching the openings of adjacent depressions or the bases of adjacent protrusions, respectively, and the depressions or protrusions, respectively, terminate in coplanar surfaces, the area of the thinned regions is taken as the sum of the areas of the coplanar surfaces. Finally, if the openings of the depressions or the bases of the protrusions are touching the openings of adjacent depressions or the bases of adjacent protrusions, respectively, and the depressions or protrusions, respectively, do not terminate in coplanar surfaces, the area of the thinned regions is taken as the sum of cross-sectional areas coplanar with the surface of the pattern roll midway between the surface of the pattern roll and the ends of the depressions or protrusions, respectively.

The thinned regions may be random in their occurrence in the film or they may be ordered or regular. For example, the thinned regions may comprise a repeating pattern having no more than about 40 lines per cm. As a further example, the thinned regions may comprise a repeating pattern having from about 40 lines per cm to about 15 lines per cm.

The film of the present invention may be used alone or it may be a component of a multilayer laminate in which one or more sheet materials are joined to the film. For example, when a single sheet material is joined to the film, such sheet material may be another film of the present invention, a film, paper, scrim, a woven fabric, a nonwoven web, or the like. For example, the sheet material may be a nonwoven web. As another example, the sheet material may be a meltblown or spunbonded nonwoven web. As a further example, the sheet material may be a spunbonded nonwoven web.

When two sheet materials are joined to the film of the present invention, such two sheet materials may be the same or different. As with the use of a single sheet material, either of the two sheet materials may be another film of the present invention, a film, paper, scrim, a woven fabric, a nonwoven web, or the like. As an example, both of the sheet materials may be nonwoven webs, such as meltblown and spunbonded nonwoven webs. As another example, both of the sheet materials may be spunbonded nonwoven webs.

More than two sheet materials may be present in a multilayer laminate, of which the film of the present invention is a component. In such case, of course, only two sheet materials may be joined to the film. When more than two sheet materials are employed, one sheet material advantageously is a scrim.

In general, the various layers of the multilayer laminate may be joined to adjacent layers by any means known to those having ordinary skill in the art. For example, the layers be joined by adhesives, such as contact adhesives, hotmelt adhesives, and the like. As another example, the layers may be joined ultrasonically. As a further example, the layers may be joined by thermal point bonding involving the application of heat and pressure. Moreover, the layers need not all be joined by the same method.

A method of preparing the above-described polyolefin film involves extruding a molten polyolefin film at a first temperature and passing the molten film through a nip which utilizes an anvil roll and a pattern roll. The anvil roll has a smooth surface. The surface of the pattern roll is maintained at a second temperature which is at least about 150° C. lower than the first temperature and selected to prevent sticking of the film to either roll. For example, the surface of the pattern roll may be maintained at a temperature of from about 10° C. to about 50° C. As another example, the surface of the pattern roll may maintained at a temperature of from about 10° C. to about 35° C. As a further example, the surface of the pattern roll may be maintained at a temperature of from about 10° C. to about 25° C.

The extrusion of the molten polyolefin film may be carded out in accordance with procedures well known to those having ordinary skill in the art. In general, the thickness of the film primarily is determined by the nip distance, i.e., the distance between the anvil roll and the pattern roll. That distance is selected to give a thickness to the film emerging from the nip of from about 0.005 mm to about 0.2 mm. Other factors affecting film thickness include the velocity of the nip, the volume of molten polymer or extrudate entering the nip which is a function of the extrusion pressure and the extrusion gap or thickness of the molten film as it emerges from the die, and the velocity of the take-up roll.

The surface of the pattern roll may have a plurality of discontinuous depressions therein, such that the area of the surface of the pattern roll lacking such depressions comprises at least about 25 percent of the surface area of the pattern roll. Alternatively, the surface of the pattern roll may have a plurality of discontinuous protrusions extending therefrom, such that the surface area of the protrusions comprises at least about 25 percent of the surface area of the pattern roll. In either case, the surface area of the depressions or protrusions is calculated as already described. The surface of the pattern roll, however, is the cylindrical surface into which the depressions extend or from which the protrusions extend and has a value which is determined solely by the diameter and length of the pattern roll. Thus, the surface area of the pattern roll is calculated as if the roll were smooth. The depression or protrusion distance is simply the distance the depressions or protrusions extend inwardly or outwardly, respectively, from the surface of the pattern roll. In other words, the depression or protrusion distance is the vertical distance of the terminal portions of the depressions or protrusions, respectively, from the surface of the pattern roll.

In addition to the area of the thinned regions, the thickness of the film also is adapted to permit the passage of steam through the film during the steam exposure step and the passage of water vapor through the film during the drying step. When depressions are present in the surface of the pattern roll, the thickness of the thinned regions is a function of the distance between the anvil roll and the pattern roll. The thickness of the film is a function of both the distance between the anvil roll and the pattern roll and the depression distance. When protrusions are present on the surface of the pattern roll, the protrusions may have a protrusion distance which is in a range of from about 15 to about 75 percent of the distance between the anvil roll and the pattern roll. Such a protrusion distance generally will result in a film in which the thickness of the thinned regions is in a range of from about 15 to about 75 percent of the thickness of the film.

If desired, at least one sheet material (as already defined) may be joined to the film after it emerges from the nip. Alternatively, two nonwoven webs may be joined to the film after it emerges from the nip.

The present invention is further described by the examples which follow. Such examples, however, are not to be construed as limiting in any way either the spirit or the scope of the present invention.

EXAMPLE 1

Polymer was extruded as a film using a commercially available pilot cast film line. The polymer was fed to an extruder and melted within the extruder by the application of heat, shear, and pressure. The molten polymer was piped into a die body and exited the die through an adjustable slice at the bottom of the die. Depending upon the polymer, the extrusion temperature typically was in a range of from about 230° C. to about 260° C. (the first temperature). The width of the die was 36 inches (about 91 cm).

The molten film then was passed through a nip located beneath the adjustable slice of the die. The nip consisted of an anvil roll and a pattern roll. The film was fed to the nip by gravity. Each roll had a length of 36 inches (about 91 cm) and a diameter of 20 inches (about 51 cm). The anvil roll had a smooth surface, whereas the surface of the pattern roll consisted of a repeating pattern of substantially identical pyramidal depressions, as illustrated by FIG. 1.

FIG. 1 shows a portion of the surface 102 of the pattern roll 100, from which three substantially identical pyramidal protrusions 104 extend. The pyramidal protrusion 104 has a base 106 and an apex 108. The base is defined by edges 110, 112, 114, and 116, with adjacent edges being at right angles to each other. Each protrusion extends from the surface 102 of the pattern roll 100 a distance 118, referred to herein as the protrusion distance. Each edge of the base 106 has a length 120, and each protrusion 104 is located a distance 122 from each adjacent protrusion. Thus, each base 106 forms a square. The area of the thinned regions is considered to be the sum of the areas of the bases of the protrusions. The actual dimensions of the protrusions are given in Table 1, with reference to FIG. 1.

TABLE 1

Protrusion Dimension Measurements

| Dimension | FIG. 1 Reference | Measurement, Inch (mm) |
| --- | --- | --- |
| Protrusion distance | 118 | 0.004 (0.102) |
| Edge of protrusion base | 120 | 0.010 (0.254) |
| Distance between protrusions | 122 | 0.002 (0.051) |

The above dimension measurements resulted in 90 lines per inch (about 35 lines per cm). The area of the thinned regions, calculated as already described, was about 30 percent of the total area of the pattern roll.

Three different polymeric materials were employed, identified as Polymers A, B, and C.

Polymer A

Polymer A was KS030 or Catalloy polypropylene, a polypropylene reactor blend of random and block copolymers and terpolymers (Himont Incorporated, Wilmington, Del.). The polymer consists of 85–92 percent by weight of polypropylene. The remainder is random or block polyethylene copolymer and random polybutylene copolymer.

Polymer B

This polymer was Escorene 3445 polypropylene (Exxon Chemical Americas, Houston, Tex.). According to the manufacturer, the polymer has a density of 0.900 g/cc and a melt flow rate of 35 g/10 minutes.

Polymer C

Polymer C was a blend consisting of 80 percent by weight of Polymer B and 20 percent by weight of Rextac® 2280 wax (Rexene Corporation, Dallas, Tex.).

Each polymer was employed to cast films having thicknesses of 0.5, 0.75, and 1.0 mil, respectively (about 0.013, 0.019, and 0.025 mm, respectively). Extrusion conditions are summarized in Table 2. The pattern roll temperature was 60°–65° F. (about 16°–18° C.).

TABLE 2

Summary of Film Extrusion Conditions

| Polymer | Extruder Pressure (psig) | Die Temp. (°C.) | Thickness Inch (mm) | Nip Speed fpm (cps) |
| --- | --- | --- | --- | --- |
| A | 1690 | 220 | 0.0005 (0.013) | 149 (76) |
|   |      |     | 0.00075 (0.019) | 138 (70) |
|   |      |     | 0.01 (0.025) | 104 (53) |
| B | 1550 | 238 | 0.0005 (0.013) | 170 (86) |
|   |      |     | 0.00075 (0.019) | 113 (57) |
|   |      |     | 0.001 (0.025) | 85 (43) |
| C | 1550 | 238 | 0.0005 (0.013) | 163 (83) |
|   |      |     | 0.00075 (0.019) | 122 (62) |
|   |      |     | 0.001 (0.025) | 82 (42) |

Each film was ultrasonically point bonded between two spunbonded polypropylene nonwoven webs, each of which had a basis weight of 34 grams per square meter (gsm). The resulting laminate or composite was used to wrap a surgical tray which was subjected to steam sterilization. Each wrapped tray was sealed with tape and placed in a sterilizer. Pressurized superheated steam was admitted into the sterilizer at a pressure of about 1 kilogram per square centimeter (kg/cm$^2$) and a temperature of about 135° C. After autoclaving, the sterilized tray was subjected to a vacuum-drying cycle. The sterilizer was an AMSCO General Purpose Sterilizer (AMSCO Division of American Sterilizer Company, Eire, Pa.).

The sterilization wraps prepared from the films made from Polymer A generally gave satisfactory results, although some melting of the film was observed. In each case, the interior of the wrapped package was dry. Wetness was observed with the wraps prepared from films made from Polymer B, however, with the amount of wetness tending to increase with increasing film thickness. Results intermediate those for Polymers A and B were observed with wraps prepared from films made from Polymer C.

EXAMPLE 2

Figure 2:
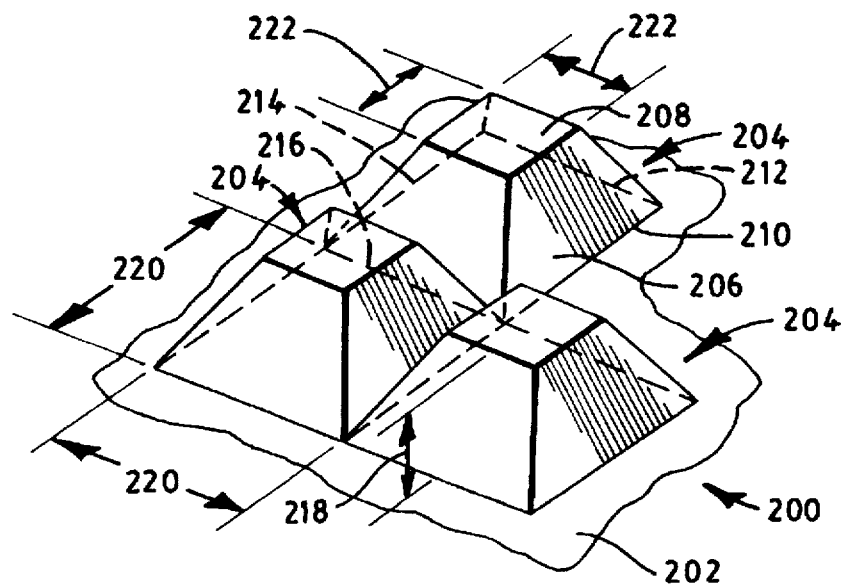
FIG. 2 is a perspective view of a portion of a second pattern roll used in the examples, illustrating truncated pyramidal protrusions on the surface of the roll.

The procedure of Example 1 was repeated, except that the surface of the pattern roll consisted of a repeating pattern of substantially identical truncated pyramidal protrusions, as illustrated by FIG. 2.

FIG. 2 shows a portion of the surface 202 of the pattern roll 200, from which three substantially identical pyramidal protrusions 204 extend. The pyramidal protrusion 204 has a base 206 and a protrusion surface 208 which is generally parallel, i.e., coplanar, with the surface 202. The base 206 is defined by edges 210, 212, 214, and 216, with adjacent edges being at right angles to each other. Each protrusion extends from the surface 202 of the pattern roll 200 a distance 218, referred to herein as the protrusion distance.

Each edge of the base 206 has a length 220. Thus, each base 206 forms a square. Each edge of the coplanar protrusion surface 208 has a length 222. Because there is no spacing between adjacent protrusions, the area of the thinned regions is deemed to be the sum of the areas of the coplanar protrusion surfaces. The actual dimensions of the protrusions are given in Table 2, with reference to FIG. 2.

TABLE 2

Protrusion Dimension Measurements

| Dimension | FIG. 2 Reference | Measurement, Inch (mm) |
|---|---|---|
| Protrusion distance | 218 | 0.008 (0.20) |
| Edge of protrusion base | 220 | 0.0224 (0.57) |
| Edge of coplanar surface | 222 | 0.0118 (0.30) |

The above dimension measurements resulted in 45 lines per inch (about 18 lines per cm). The area of the thinned regions, calculated as already described, was about 28 percent of the total area of the pattern roll.

Two polymers were studied, Polymer A and Polymer B, described above. Extrusion conditions are summarized in Table 3. Again, the pattern roll temperature was 60°–65° F. (about 16°–18° C.).

TABLE 3

Summary of Film Extrusion Conditions

| Polymer | $TiO_2$ Wt. - % | Extruder Pressure (psig) | Die Temp. (°C.) | Thickness Inch (mm) | Nip Speed fpm (cps) |
|---|---|---|---|---|---|
| A | 0 | 670 | 216 | 0.001 (0.025) | 104 (53) |
|   |   |   |   | 0.00075 (0.019) | 138 (70) |
|   |   |   |   | 0.0005 (0.013) | 208 (106) |
| A | 5 | 670 | 216 | 0.001 (0.025) | 104 (53) |
|   |   |   |   | 0.00075 (0.019) | 138 (70) |
|   |   |   |   | 0.0005 (0.013) | 208 (106) |
| A | 10 | 660 | 214 | 0.001 (0.025) | 104 (53) |
|   |   |   |   | 0.00075 (0.019) | 138 (70) |
|   |   |   |   | 0.0005 (0.013) | 208 (106) |
| B | 0 | 580 | 218 | 0.001 (0.025) | 106 (54) |
|   |   |   |   | 0.00075 (0.019) | 141 (72) |
| B | 5 | 580 | 218 | 0.001 (0.025) | 106 (54) |
|   |   |   |   | 0.00075 (0.019) | 141 (72) |

The sterilization wraps prepared from the films made from both Polymers A and B generally gave satisfactory results. In each case, the interior of the wrapped package was dry.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A multilayer laminate useful as a sterilization wrap material, one layer of which is a polyolefin film having a thickness of from about 0.005 mm to about 0.2 mm and a plurality of discontinuous thinned regions whereby the thickness and area of the thinned regions are adapted to permit the passage of steam and water vapor through the film during steam sterilization.

2. The laminate of claim 1, in which the film is joined to a nonwoven web.

3. The laminate of claim 2, in which the nonwoven web is a spunbonded nonwoven web.

4. The laminate of claim 1, in which the film is joined to and located between two nonwoven webs.

5. The laminate of claim 4, in which the nonwoven webs are selected independently from meltblown nonwoven webs and spunbonded nonwoven webs.

6. The laminate of claim 5, in which both nonwoven webs are spunbonded nonwoven webs.

7. A sterilization wrap comprising the laminate of claim 1.

8. A sterilization wrap comprising the laminate of claim 2.

9. A sterilization wrap comprising the laminate of claim 4.

10. A sterilization wrap comprising the laminate of claim 6.

11. A medical garment comprising the laminate of claim 1.

12. A medical garment comprising the laminate of claim 2.

13. A medical garment comprising the laminate of claim 4.

* * * * *